(12) United States Patent
Rothstein et al.

(10) Patent No.: US 12,011,471 B2
(45) Date of Patent: Jun. 18, 2024

(54) EXTRACTS ENRICHED WITH POLYPHENOLIC COMPOUNDS AND RELATED METHODS

(71) Applicant: ATLAS365 INCORPORATED, Mississauga (CA)

(72) Inventors: Steven Rothstein, Guelph (CA); Tariq Akhtar, Guelph (CA); Jose Casaretto, Guelph (CA); Gale Bozzo, Guelph (CA); Colby Perrin, Guelph (CA); Cameron Parry, Guelph (CA)

(73) Assignee: ATLAS365 INCORPORATED, Mississauga (CA)

( * ) Notice: Subject to any disclaimer, the term of this patent is extended or adjusted under 35 U.S.C. 154(b) by 21 days.

(21) Appl. No.: 17/787,240

(22) PCT Filed: Dec. 18, 2020

(86) PCT No.: PCT/CA2020/051744
§ 371 (c)(1),
(2) Date: Jun. 17, 2022

(87) PCT Pub. No.: WO2021/119826
PCT Pub. Date: Jun. 24, 2021

(65) Prior Publication Data
US 2023/0047321 A1 Feb. 16, 2023

Related U.S. Application Data

(60) Provisional application No. 62/950,293, filed on Dec. 19, 2019.

(51) Int. Cl.
*A61K 36/185* (2006.01)
*A61K 31/05* (2006.01)
(Continued)

(52) U.S. Cl.
CPC ............ *A61K 36/185* (2013.01); *A61K 31/05* (2013.01); *B01D 15/1871* (2013.01); *B01J 20/265* (2013.01)

(58) Field of Classification Search
None
See application file for complete search history.

(56) References Cited

U.S. PATENT DOCUMENTS 9,730,911 B2    8/2017  Verzura et al.
2010/0222437 A1 9/2010  Munoz Blanco et al.
(Continued)

FOREIGN PATENT DOCUMENTS

CN    102307983 A    1/2012
CN    108083989 A    5/2018
(Continued)

OTHER PUBLICATIONS

Barrett, M.L. et al., "Cannflavin A and B, prenylated flavones from *Cannabis sativa* L.," Experientia, 42:452-453, (1986).
(Continued)

*Primary Examiner* — Michael V Meller
(74) *Attorney, Agent, or Firm* — Alston & Bird LLP (57) ABSTRACT

In aspects, a cannabis extract enriched in polyphenolic compounds is provided herein. Also provided herein is a method for enriching a composition with polyphenolic compounds as well as compositions made by the method. Various cosmetic and pharmaceutical products, methods, and uses are provided herein as well as natural health products.

12 Claims, 5 Drawing Sheets

(51) Int. Cl.
  *B01D 15/18*  (2006.01)
  *B01J 20/26*  (2006.01)

(56) References Cited

U.S. PATENT DOCUMENTS

2016/0106705 A1  4/2016  Verzura et al.
2019/0010106 A1  1/2019  Oroskar et al.

FOREIGN PATENT DOCUMENTS

CN        110066216 A     7/2019
WO     WO 2016/064987 A1  4/2016

OTHER PUBLICATIONS

Barrett, M.L. et al., "Isolation from *Cannabis sativa* L. of cannflavin—a novel inhibitor of prostaglandin production," Biochem. Pharmacol, 34(11):2019-224, (Jun. 1, 1985).

Cosmetics Alliance Canada website. "FAQ: What You Need to Know about Cannabis and Personal Care Products," Aug. 27, 2019, Cosmetics Alliance Canada Website, 13 pgs., [Retreived from the Internet on Mar. 5, 2021: <<https://cosmeticsalliance.ca/need-know-cannabis-personal-care-products/>>].

Elsohly, H.N. et al., "Constituents of *Cannabis sativa* L. XXII: isolation of spiro-indan and dihydrostilbene compounds from a Panamanian variant grown in Mississippi, United States of America," United Nations: Office on Drug and Crime, 5 pgs., [Retreived from the Internet on Mar. 4, 2021: <<https://www.unodc.org/unodc/en/data-and-analysis/bulletin/bulletin_1982-01-01_2_page005.html>>].

Izzo, L. et al., "Analysis of Phenolic Compounds in Commercial *Cannabis sativa* L. Inflorescences Using UHPLC-Q-Orbitrap HRMS," Molecules, 25(3):631, (Jan. 31, 2020).

Rasouli, H., "Polyphenols and their benefits: A review," International Journal of Food Properties, 20(2):1700-1741, (Dec. 21, 2017).

Smeriglio, A., "Polyphenolic Compounds and Antioxidant Activity of Cold-Pressed Seed Oil from Finola Cultivar of *Cannabis sativa* L," Phytother. Res., 30(8):1298-1307, (Aug. 2016).

WIPO Application No. PCT/CA2020/051744, PCT International Preliminary Report on Patentability mailed May 17, 2022.

WIPO Application No. PCT/CA2020/051744, PCT International Search Report and Written Opinion of the International Searching Authority mailed Mar. 8, 2021.

Ganesh, Linitha, "FAQ_What you Need to Know About Cannabis and Personal Care Products—Cosmetics Alliance Canada," 1-11, (Aug. 27, 2019). [Retrieved from the Internet Aug. 27, 2019: <URL:https://www.cosmeticsalliance.ca/need-know-cannabis-personal-care-products/>].

Mei, Quanxi, Incense Medicine—Agilawood, Quercetin, 2 pgs., (Jun. 20, 2023), Eng. Transl. attached.

Xiang, Hongding, Celery Promotes Sugar Utilization, Diabetes Diet and Exercise, 2 pgs., (Jun. 20, 2023), Eng. Transl. attached.

CN Application No. 202080096542.7, First Office Action mailed Jun. 29, 2023.

EP Application No. 20901264.0, Communication Pursuant to Rule 164(1) EPC mailed Dec. 4, 2023.

EP Application No. 20901264.0, Supplementary European Search Report mailed Feb. 26, 2024.

Figure 5

EXTRACTS ENRICHED WITH POLYPHENOLIC COMPOUNDS AND RELATED METHODS

CROSS-REFERENCE TO RELATED APPLICATIONS

This application is a national stage entry of International Application No. PCT/CA2020/051744 filed Dec. 18, 2020, which claims the benefit of U.S. provisional application No. 62/950,293 filed Dec. 19, 2019, which is hereby incorporated by reference.

FIELD

The present invention relates to extracts. More specifically, the present invention is, in embodiments, concerned with extracts enriched in polyphenolic compounds and related products, methods, and uses.

BACKGROUND

Plants are rich in bioactive natural compounds that are able to modulate one or more cellular processes, thus having effects on human health. These compounds, commonly known as phytochemicals, have reached a special place in drug discovery for the treatment of a vast number of medical conditions, including cancer, immunological disorders, infectious diseases, chronic diseases, and metabolic disorders.

A large group of phytochemicals consists of phenolic compounds. These are secondary metabolites biosynthesized by all plants for their optimal growth and development as well as for coping with changing environmental conditions. They provide defense against predators, as volatile attractants towards the same or other species, or as coloring agents to attract or warn other species. Phenols and polyphenols, which also include the flavonoids group, also act as antioxidants for protecting plants against oxidative stress and for their survival in UV light rich environments. Plenty of scientific data support the hypothesis that these natural antioxidant phytochemicals found in food and in their pure form benefit consumers, and therefore they have become important actors in the nutraceutical industry.

Several techniques for the extraction, isolation and purification of phenolic compounds from complex mixtures and plant tissues are often used. Liquid-liquid extraction and column chromatographic procedures are the main conventional techniques for extraction and separation of phytochemicals. Some of them, such as semi-preparative high-performance liquid chromatography, supercritical fluid extraction, high-speed counter-current liquid chromatography, precipitation—adsorption and solid-phase extraction (Watson, 2014), have the disadvantages of being time-consuming and allowing small volumes of sample. In addition, some methods require a high investment cost and allow low polyphenols yields.

There is a need for alternative therapies to overcome or mitigate at least some of the deficiencies of the prior art, and/or to provide a useful alternative.

DESCRIPTION OF THE DRAWINGS

The present invention will be further understood from the following description with reference to the Figures, in which.

SUMMARY

In accordance with an aspect, there is provided a cannabis extract enriched in polyphenolic compounds.

In an aspect, the extract is substantially free of THC.

In an aspect, the extract comprises less than about 5%, 4%, 3%, 2%, 1%, 0.5%, or 0.1% of THC.

In an aspect, the extract is substantially free of cannabinoids, or wherein the extract comprises less than about 5%, 4%, 3%, 2%, 1%, 0.5%, or 0.1% of cannabinoids.

In an aspect, the extract is substantially free of cannabidiol, or wherein the extract comprises less than about 5%, 4%, 3%, 2%, 1%, 0.5%, or 0.1% of cannabidiol.

In an aspect, the extract is substantially free of terpenes, or wherein the extract comprises less than about 5%, 4%, 3%, 2%, 1%, 0.5%, or 0.1% of terpenes.

In an aspect, the extract comprises THC.

In an aspect, the extract comprises a cannabinoid.

In an aspect, the extract comprises cannabidiol.

In an aspect, the extract comprises a terpene.

In an aspect, the extract is from *Cannabis sativa* L. marijuana or hemp.

In an aspect, the extract is from a plant material comprising a leaf, a root, a stem, a branch, a flower, an inflorescence, a fruit, a seed, a cell, a tissue culture, or a combination thereof.

In an aspect, the polyphenolic compounds comprise flavonoids, stilbenes and/or bibenzyls.

In an aspect, the flavonoids, comprise cannflavin A, cannflavin B, or a combination thereof.

In an aspect, the bibenzyls comprise canniprene.

In accordance with an aspect, there is provided a method for producing a composition enriched with polyphenolic compounds, the method comprising applying the composition to an adsorption resin and eluting the adsorption resin to produce an eluent enriched with polyphenolic compounds.

In an aspect, the adsorption resin comprises a macroporous adsorption resin and/or PVPP.

In an aspect, the method comprises:
applying the composition to a first adsorption resin and eluting the first adsorption resin to produce a first eluent enriched with polyphenolic compounds; and
applying the first eluent to a second adsorption resin and eluting 5 the second adsorption resin to produce a second eluent enriched with polyphenolic compounds.

In an aspect, the first adsorption resin comprises a macroporous adsorption resin and the second adsorption resin comprises PVPP.

In an aspect, the first adsorption resin comprises PVPP and the second adsorption resin comprises a macroporous adsorption resin.

In an aspect, the macroporous adsorption resin comprises a polymeric non-ionic polystyrene-divinylbenzene resin such as SP825, SP207, XAD-16, or a combination thereof.

In an aspect, eluting the macroporous adsorption resin comprises adding about 3 to about 4 volumes of about 60 to about 100% ethanol.

In an aspect, eluting the PVPP adsorption resin comprises adding about 3 to about 4 volumes of about 70 to about 100% ethanol.

In an aspect, the ethanol has a pH of about 9.0.

In an aspect, the composition comprises a plant extract.

In an aspect, the plant extract is a cannabis extract.

In an aspect, the extract is substantially free of THC.

In an aspect, the extract comprises less than about 5%, 4%, 3%, 2%, 1%, 0.5%, or 0.1% of THC.

In an aspect, the extract is substantially free of cannabinoids, or wherein the extract comprises less than about 5%, 4%, 3%, 2%, 1%, 0.5%, or 0.1% of cannabinoids.

In an aspect, the extract is substantially free of cannabidiol, or wherein the extract comprises less than about 5%, 4%, 3%, 2%, 1%, 0.5%, or 0.1% of cannabidiol.

In an aspect, the extract is substantially free of terpenes, or wherein the extract comprises less than about 5%, 4%, 3%, 2%, 1%, 0.5%, or 0.1% of terpenes.

In an aspect, the extract comprises THC.

In an aspect, the extract comprises a cannabinoid.

In an aspect, the extract comprises cannabidiol.

In an aspect, the extract comprises a terpene.

In an aspect, the extract is from *Cannabis sativa* L. marijuana or hemp.

In an aspect, the extract is from a plant material comprising a leaf, a root, a stem, a branch, a flower, an inflorescence, a fruit, a seed, a cell, a tissue culture, or a combination thereof.

In an aspect, the polyphenolic compounds in the extract comprise flavonoids, stilbenes, and/or bibenzyls.

In an aspect, the flavonoids in the extract comprise cannflavin A, cannflavin B, or a combination thereof.

In an aspect, the bibenzyls in the extract comprise canniprene.

In an aspect, the method further comprises extracting the plant material with a polar solvent prior to applying the extract to the adsorption resin.

In an aspect, the polar solvent comprises ethanol, methanol, isopropanol, acetone, acetonitrile, or 5 combinations thereof.

In an aspect, the plant material is dried and optionally ground to a powder, such as a coarse powder, prior to extraction.

In an aspect, the extracting comprises mixing the plant material with the polar solvent and incubating the mixture for a time.

In an aspect, the time is from about 12 to about 24 hours.

In an aspect, the incubating is at a temperature of from about 4° C. to about 20° C.

In an aspect, the extracting is repeated at least once, such as 1, 2, 3, 4, 5, 6, 7, 8, 9, or 10 times.

In an aspect, the method further comprises dealcoholizing and concentrating the eluent.

In an aspect, dealcoholizing and concentrating the eluent is carried out under reduced pressure at about 40° C. to about 80° C.

In accordance with an aspect, there is provided a method described herein are for at least partially purifying cannflavin A, cannflavin B and/or canniprene.

In accordance with an aspect, there is provided a composition enriched in polyphenolic compounds made by a method described herein.

In accordance with an aspect, there is provided a cosmetic, pharmaceutical, and/or natural health product comprising the cannabis extract or the composition described herein.

In an aspect, the cannabis extract or the composition described herein is for use as cosmetic, pharmaceutical, and/or natural health product.

In accordance with an aspect, there is provided a cosmetic method comprising administering the cannabis extract or the composition described herein to a subject.

In accordance with an aspect, there is provided a method of treating and/or preventing inflammation, the method comprising administering the cannabis extract or the composition described herein to a subject in need thereof.

In accordance with an aspect, there is provided a method of treating and/or preventing cancer, the method comprising administering the cannabis extract or the composition described herein to a subject in need thereof.

In accordance with an aspect, there is provided a method of treating and/or preventing atherosclerosis, the method comprising administering the cannabis extract or the composition described herein to a subject in need thereof.

In accordance with an aspect, there is provided a method of hepatoprotection, the method comprising administering the cannabis extract or the composition described herein to a subject in need thereof.

In accordance with an aspect, there is provided a use of the cannabis extract or the composition described herein for cosmetic purposes.

In accordance with an aspect, there is provided a use of the cannabis extract or the composition described herein for treating and/or preventing inflammation.

In accordance with an aspect, there is provided a use of the cannabis extract or the composition described herein for treating and/or preventing cancer.

In accordance with an aspect, there is provided a use of the cannabis extract or the composition described herein for treating and/or preventing atherosclerosis.

In accordance with an aspect, there is provided a use of the cannabis extract or the composition described herein for hepatoprotection.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION

Described herein are low-cost and safe methods for preparing a polyphenol-enriched extract from cannabis, wherein the product prepared has trace or undetectable amounts of cannabinoids.

Definitions

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning. A Laboratory Manual, Cold Springs Harbor Press (Cold Springs Harbor, N Y 1989), each of which are incorporated herein by reference. For the purposes of the present invention, the following terms are defined below.

The term "endogenous" as used herein refers to any polynucleotide or polypeptide which is present and/or naturally expressed within a particular species or cell thereof.

"Isolated" refers to a molecule that has been purified from its source or has been prepared by recombinant or synthetic methods and purified. Purified polypeptides are substantially free of contaminating components, such as THC, cannabinoids, and/or terpenes, for example.

"Substantially free" herein means less than about 5%, typically less than about 2%, more typically less than about 1%, even more typically less than about 0.5%, most typically less than about 0.1% contamination, such as with THC, cannabinoids, and/or terpenes.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as inflammation, or may render the inflammation more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat inflammation. Effective amounts of the polyphenolic compounds described herein may vary according to factors such as the disease state, age, sex, and weight of the subject. Dosage or treatment regimes may be adjusted to provide the optimum therapeutic response, as is understood by a skilled person.

Likewise, an "effective amount" of the polyphenolic compounds described herein refers to an amount sufficient to function as desired, such as to treat inflammation.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

"Carriers" as used herein include cosmetically or pharmaceutically acceptable carriers, excipients, or stabilizers that are nontoxic to the cell or subject being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any embodiments described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in embodiments, THC, cannabinoids, and/or terpenes are explicitly excluded from the compositions and methods described herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compositions

Described herein are cannabis extracts enriched in polyphenolic compounds.

Typically, the extracts comprise at least about 50% polyphenolic compounds, such as at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5%, or at least about 99.9% polyphenolic compounds. The extracts described herein are typically substantially free of THC, cannabinoids, such as cannabidiol, and/or terpenes. Such THC-, cannabinoid-, cannabidiol-, and/or terpene-free compositions comprise, for example, less than about 5%, about 4%, about 3%, about 2%, about 1%, about 0.5%, about 0.1%, or about 0.01% THC, cannabinoid, cannabidiol, and/or terpene by weight. In other aspects, the extracts described herein comprise or are combined with THC, cannabinoids such as cannabidiol, and/or terpenes.

The extracts described herein are derived from any cannabis species, including marijuana and hemp. For example, *Cannabis sativa, Cannabis indica, Cannabis ruderalis*, and any combinations thereof may serve as the source of the extract. Typically, the extracts are derived from *Cannabis sativa* L. Use of any individual strain or combinations of strains within any species or combination of species is also contemplated. Similarly, it will be understood that the extracts may be derived from any plant source, including a leaf, a root, a stem, a branch, a flower, an inflorescence, a fruit, a seed, a cell, a tissue culture, or a combination thereof.

There are over 5000 naturally occurring flavonoids in plants. Their chemical nature depends on their structural class (flavanols, flavones, flavonols, flavanones, isoflavones, anthocyanins; Table 1), degree of hydroxylation and conjugations, which in turn dictate their antioxidant and pharmacological activities. Flavonoids have extensive biological properties that promote human health and help reduce the risk of diseases (Kikuchi et al., 2019; Kumar & Pandey, 2013; Rasouli et al., 2017; Shama et al., 2016). Different plant sources may provide different profiles of polyphenolic compounds in the extracts.

TABLE 1

Chemical structure of flavonoids

| Group of flavanoid | Structure backbone | Examples | | | |
|---|---|---|---|---|---|
| Flavones | [structure] | Luteolin | Apigenin | Chrysin | |
| Flavonols | [structure] | Quercetin | Kaempferol | Galangin | |
| Flavanones | [structure] | Hesperetin | Naringenin | | |

TABLE 1-continued

Chemical structure of flavonoids

| Group of flava-noid | Structure backbone | Examples |
|---|---|---|
| Flava-nonol | (structure) | Taxifolin |
| Iso-flavones | (structure) | Genistein, Daidzein |
| Flavan-3-ols | (structure) | Catechin, Epicatechin |

In cannabis, the distribution of flavonoids and phenolic compounds is variable between strains and diverse from one plant tissue to another (Flores-Sanchez & Verpoorte, 2008). The content of some flavonoids is higher in seedlings and fruits compared to leaves while others are more abundant in leaves and seedlings. Quercetin and luteolin, for example, have higher contents in male flowers than in leaves, while kaempferol is more concentrated in female flowers than in fruits. Also, apigenin contents are significantly different between flower genders. Therefore, cannabis phenolics can be isolated and detected in several parts of the mature plant. One disregarded group of phenolic compounds present in cannabis is the stilbenoids (Table 2), totaling over 25 different molecules (Pollastro et al., 2018). These comprise a small group of compounds characterized by an 1,2-diphenylethylene (stilbene) backbone as well as related structures such as bibenzyls, dihydrostilbenes, phenanthrenes, 9,10-dihydriphenanthrenes and related prenylated, geranylated and glycosylated derivatives. Of the eight dihydrostibenes reported in cannabis, half are prenylated forms: 3,4'-dihydroxy-5,3'-dimethoxy-5' isoprenyl bibenzyl, and canniprene, cannabistilbene I, cannabistilbene IIa, IIb. In addition, over 20 different flavonoids have also been identified in cannabis. These include apigenin, luteolin, quercetin, kaempferol, cannflavin A, cannflavin B, ß-sitosterol, vitexin, isovitexin, kaempferol, and orientin (Andre et al., 2016; Flores-Sanchez & Verpoorte, 2008), and they appear as methylated and prenylated aglicones or as 0-glycosides or C-glycosides conjugated. Of those, the prenylated aglicone flavones cannflavins are unique to cannabis. They were first identified in the 1980s and were proved to have potent anti-inflammatory activity (Barrett et al 1985). Before their biosynthetic pathway in cannabis was identified (Rea et al., 2019), cannflavins, as well as other cannabis polyphenols, have been obtained primarily through extraction from plant material.

TABLE 2

Chemical structure of stilbenoids and bibenzyls

| Structure backbone | Examples |
| --- | --- |
| Stilbenoid | Resveratrol, Pterostilbene |
| Bibenzyl | Dihydroresveratrol, Dihydropiceatannol |

Thus, typically, the extracts described herein comprise flavonoids, stilbenes, and/or bibenzyls. In certain aspects, the flavonoids comprise cannflavin A and/or cannflavin B. In certain aspects the bibenzyls comprise canniprene. In aspects, the extracts are enriched with cannflavin A, cannflavin B and/or canniprene.

The compositions may be formulated for use by a subject, such as a mammal, including a human. Compositions comprising the polyphenolic compounds described herein may comprise about 0.00001% to about 99% by weight of the active and any range there-in-between, such as from about 0.00001%, about 0.0001%, about 0.001%, about 0.01%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.7%, or about 99.9%, to about 0.0001%, about 0.001%, about 0.01%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.7%, about 99.9%, about 99.99%. For example, typical doses may comprise from about 0.1 μg to about 100 μg of the molecules described herein per 300 mg dose, such as about 0.5 μg, about 1 μg, about 2 μg, about 3 μg, about 4 μg, about 5 μg, about 6 μg, about 7 μg, about 8 μg, about 9 μg, about 10 μg, about 25 μg, about 50 μg, or about 75 μg per 300 mg dose, such as from about 0.1 μg to about 10 μg, or from about 1 μg to about 5 μg, or from about 1 μg to about 2 μg per 300 mg dose (and all related increments and percentages by weight).

The compositions described herein may be used in any suitable amount, but are typically provided in doses comprising from about 1 to about 10000 ng/kg, such as from about 1 to about 1000, about 1 to about 500, about 10 to about 250, or about 50 to about 100 ng/kg, such as about 1, about 10, about 25, about 50, about 75, about 100, about 150, about 200, about 250, about 300, or about 500 ng/kg. In other aspects, the compositions described herein are provided in doses of from about 1 to about 10000 mg per dose, such as from about 1 to about 1000, about 1 to about 500, about 10 to about 250, or about 50 to about 100 mg, such as about 1, about 10, about 25, about 50, about 75, about 100, about 150, about 200, about 250, about 300, about 400, about 500 mg, about 600 mg, about 700 mg, about 800 mg, about 900 mg, or about 1000 mg. For example, in some aspects, canniprene is provided at about 100 mg per dose, cannflavin A is provided at about 500 mg per dose, and cannflavin B is provided at about 400 mg per dose. In aspects, canniprene, cannflavin A, and cannflavin B are provided together in a ratio, such as a ratio of about 1:5:4.

In other aspects, the compositions described herein are dosed so as to obtain about a 0.01 μM to about a 100 μM target concentration in blood of a human, such as from about 0.01 μM, about 0.05 μM, about 0.1 μM, about 0.2 μM, about 0.3 μM, about 0.4 μM, about 0.5 μM, about 0.6 μM, about 0.7 μM, about 0.8 μM, about 0.9 μM, about 1 μM, about 2 μM, about 3 μM, about 4 μM, about 5 μM, about 6 μM, about 7 μM, about 8 μM, about 9 μM, about 10 μM, about 20 μM, about 30 μM, about 40 μM, about 50 μM, about 60 μM, about 70 μM, about 80 μM, or about 90 μM to about 0.05 μM, about 0.1 μM, about 0.2 μM, about 0.3 μM, about 0.4 μM, about 0.5 μM, about 0.6 μM, about 0.7 μM, about 0.8 μM, about 0.9 μM, about 1 μM, about 2 μM, about 3 μM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, or about 100 µM. For example, typically canniprene is dosed so as to obtain about a 0.4 µM target concentration, cannflavin A is dosed so as to obtain about a 2 µM target concentration, and cannflavin B is dosed so as to obtain about a 2 µM target concentration.

The compositions may be administered over a period of hours, days, weeks, or months, depending on several factors, including the severity and type of the inflammation or other condition being treated, whether a recurrence is considered likely, or to prevent the inflammation or other condition, etc. The administration may be constant, e.g., constant infusion over a period of hours, days, weeks, months, etc. Alternatively, the administration may be intermittent, e.g., the molecules may be administered once a day over a period of days, once an hour over a period of hours, or any other such schedule as deemed suitable.

The compositions described herein can be prepared by per se known methods for the preparation of pharmaceutically or cosmetically acceptable compositions which can be administered to subjects, such that an effective quantity of the active substance is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456 (the entirety of which is incorporated herein by reference).

Pharmaceutically acceptable carriers are well known to those skilled in the art and include, for example, sterile saline, lactose, sucrose, calcium phosphate, gelatin, dextrin, agar, pectin, peanut oil, olive oil, sesame oil, cannabis oil, and water. Furthermore the composition may comprise one or more stabilizers such as, for example, carbohydrates including sorbitol, mannitol, starch, sucrose, dextrin and glucose, proteins such as albumin or casein, and buffers like alkaline phosphates.

The compositions described herein can, in embodiments, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, intravaginal, aerosol, oral, topical, or transdermal administration. Typically, the compositions of the invention are administered orally or topically directly to a site of inflammation or in a cosmetic oil, lotion, cream, or gel to a desired body location, such as the face.

It is understood by one of skill in the art that the compositions described herein can be used in conjunction with known therapies for prevention and/or treatment of inflammation in subjects and/or with compositions for preventing the signs of aging or other cosmetic compositions. Similarly, the compositions described herein can be combined with one or more other cannabis-derived products, such as cannabinoids, terpenes, or THC. The compositions described herein may, in embodiments, be administered in combination, concurrently or sequentially, with conventional treatments for inflammation or other conditions, including non-steroidal anti-inflammatory drugs, for example. The compositions described herein may be formulated together with such conventional treatments when appropriate.

Because the compositions described herein are enriched in polyphenolic compounds, they are expected to exhibit activities associated with those compounds. Thus, the compositions described herein may exhibit a number of different activities, including, for example:

Antioxidant activity. This is the best-described property of almost every group of flavonoids, stilbenoids and bibenzyls, which depends upon the arrangement of functional groups around the rings' structure. Functional hydroxyl groups in flavonoids mediate their antioxidant effects by scavenging free radicals and/or by chelating metals, which is crucial in the prevention of radical generation that damages target biomolecules.

Antiatherosclerotic effects. Flavonoids are likely to influence the vascular system due to their antioxidant properties by scavenging free oxygen radicals that oxidize LDLs known to damage the endothelial wall and thereby preventing atherosclerotic alterations.

Anti-inflammatory activity. Inflammation is a normal biological process in response to tissue injury, chemical irritation or pathogen infection. This process is initiated by the migration of immune cells from blood vessels and release of mediator molecules at the site of damage, and then followed by the release of reactive oxygen and nitrogen species (ROS and RNS), and pro-inflammatory cytokines to repair injured tissues. In general, normal inflammation is rapid and self-limiting, but abnormal resolution and prolonged inflammation cause various chronic disorders. Some flavonoids have a significant effect on the function of the immune system and inflammatory cells. A number of them such as hesperidin, apigenin, luteolin, and quercetin are reported to possess anti-inflammatory and analgesic effects. The mode of action of flavonoids in this process varies: they may inhibit the function of enzyme systems critically involved in the generation of inflammatory processes (especially tyrosine and serine-threonine protein kinases); they are able to inhibit expression of nitric oxide synthase, cyclooxygenase, and lipooxygenase, which are responsible for the production of a great amount of nitric oxide, prostanoids, leukotrienes, and other mediators of the inflammatory process such as cytokines, chemokines, or adhesion molecules. Much of their anti-inflammatory effect is on the biosynthesis of protein cytokines that mediate adhesion of circulating leukocytes to sites of injury. Certain flavonoids, stilbenoids and bibenzyls are also potent inhibitors of the production of prostaglandins, a group of powerful pro-inflammatory signaling molecules.

Anticancer activity. Flavonoids present in fruits and vegetables have been reported as cancer chemopreventive agents. Consumption of the flavonol quercetin is inversely associated with the incidence of prostate, lung, stomach, and breast cancers. Ingestion of resveratrol also seems to lower the risk of developing lung, endometrium, esophagus, stomach, and colon cancers. Different cellular inhibitory activities are amongst the proposed mechanisms by which flavonoids have an effect on the initiation and promotion stages of carcinogenicity.

Antibacterial activity. Pure flavonoids (apigenin, galangin, flavone and flavonol glycosides, isoflavones, flavanones, catechins, and chalcones) and flavonoid-rich plant extracts from different species have been reported to be effective antimicrobial substances against a wide array of microorganisms in vitro. Their mode of action may be related to their ability to inactivate microbial adhesins, enzymes, or cell envelope transport proteins.

Antiviral activity. Naturally occurring flavonoids with antiviral activity have been recognized for years and most studies have focused on their activity around the inhibition of various enzymes associated with the life cycle of viruses. For example, flavan-3-ol and the flavones-glucoside baicalin were shown to be effective in the selective inhibition of infection and replication of HIV-1, HIV-2, and similar immunodeficiency virus infections. Other compounds such as quercetin, rutin, apigenin, naringenin, luteolin, and galangin were shown to present activity against rabies, herpes, polio, or parainfluenza viruses.

Hepatoprotective activity. Several flavonoids such as catechin, apigenin, quercetin, naringenin, rutin, and venoruton have been reported for their hepatoprotective activities.

Methods of Production

Also described herein are methods for producing compositions enriched in polyphenolic compounds, such as flavonoids, such as cannflavin A and/or cannflavin B. Typically, the methods comprise applying the composition to an adsorption resin, optionally in a chromatography column, and eluting the adsorption resin. The resulting eluent is enriched with polyphenolic compounds.

Typically, the adsorption resin comprises a macroporous adsorption resin and/or PVPP. It will be understood that the composition could be applied to a single such adsorption resin, to a mixture of different adsorption resins, or to one adsorption resin following by one or more additional adsorption resins or further chromatographic or other purification steps.

For example, in specific aspects, the method comprises applying the composition to a first adsorption resin and eluting the first adsorption resin to produce a first eluent enriched with polyphenolic compounds and subsequently applying the first eluent to a second adsorption resin and eluting the second adsorption resin to produce a second eluent enriched with polyphenolic compounds. The first and second adsorption resins may be the same or different and this process can be repeated as many times as desired until the composition is sufficiently enriched.

In typical aspects, the method comprises applying the composition to a macroporous adsorption resin and eluting the macroporous adsorption resin to produce a first eluent enriched with polyphenolic compounds and subsequently applying the first eluent to a PVPP adsorption resin and eluting the PVPP adsorption resin to produce a second eluent enriched with polyphenolic compounds. Alternatively, the method comprises applying the composition to a PVPP adsorption resin and eluting the PVPP adsorption resin to produce a first eluent enriched with polyphenolic compounds and subsequently applying the first eluent to a macroporous adsorption resin and eluting the macroporous adsorption resin to produce a second eluent enriched with polyphenolic compounds.

Examples of macroporous adsorption resins include polymeric non-ionic polystyrene-divinylbenzene resins such as SP825, SP207, and XAD-16. Combinations of resins are also contemplated.

The composition applied to the adsorption resin is typically an aqueous composition and the elution is typically carried out with a lower alcohol such as methanol, ethanol, propanol, etc. Typically ethanol is used. The alcohol may be at 100% concentration or it may be diluted to 50% or more, such as from about 50%-100% or from about 60% to 100%, or from about 70% to 100%. The alcohol may be pH-adjusted to a desired value, such as an acidic, neutral, or alkaline value, typically an alkaline value, such as about 8, 9, or 10, such as about 9.0.

Generally, the eluting step involves applying an amount of the lower alcohol to the adsorption resin and collecting the eluent. The amount of lower alcohol applied is generally at least about 1, 2, 3, 4, 5, or 6 volumes relative to the volume of the adsorption resin or the composition initially applied.

In more specific aspects, a typical capture step uses resin beads with large surface areas to increase adsorption capacities, however, in the case of less hydrophilic polyphenols, some resins may not get saturated because of the low concentrations of the desired polyphenols. One strategy is to incorporate a step that involves the use of a resin that has an increased affinity toward polyphenols and gets more easily saturated at much lower concentrations.

Both the macroporous adsorption resin and the PVPP resins described herein are separation and purification techniques often used in industrial production. Because their separation principles are different, the separation effects of them complement each other. Combining these two resins results in a more efficient extraction of the desired polyphenol fraction.

Following the enrichment steps described herein, the resulting eluent is typically alcoholized and concentrated, for example, in a rotavapor under reduced pressure at 40-80° C. to obtain a thick substance.

The composition applied to the adsorption resin may be derived from any desired source. Typically the composition comprises a plant extract, which is optionally from a cannabis plant of any species or strain, such as *Cannabis sativa* L. and it may be described as marijuana or hemp. The plant material that is extracted, whether cannabis or another plant, may comprise, for example, a leaf, a root, a stem, a branch, a flower, an inflorescence, a fruit, a seed, a cell, a tissue culture, or a combination thereof.

As described above, the extract may comprise THC or, more typically, it is substantially free of THC. In aspects, the extract comprises less than about 5%, 4%, 3%, 2%, 1%, 0.5%, or 0.1% of THC. In additional or alternative aspects, the extract may comprise cannabinoids, such as cannabidiol, or it may be substantially free of cannabinoids or cannabidiol, such as less than about 5%, 4%, 3%, 2%, 1%, 0.5%, or 0.1% of cannabinoids or cannabidiol. In additional or alternative aspects, terpenes may be present in the extracts or the extract may be substantially free of terpenes or may comprise less than about 5%, 4%, 3%, 2%, 1%, 0.5%, or 0.1% of terpenes.

Prior to applying the extract to the adsorption resin, the method in aspects further comprises extracting a plant material with a polar solvent. Polar solvents, many of which are available in food-grade quality, provide improved extraction for natural compounds that can be used and consumed by people. Polar solvents are low molecular weight solvents and include but are not limited to ethanol, methanol, isopropanol, acetone, or acetonitrile. Generally, the polar solvent is itself soluble in water. Typically, the polar solvent is ethanol. Polar, water-miscible solvents combined at relatively high temperatures (40° C. to 80° C.) and at atmospheric pressure, allow efficient and cost-effective extraction of polyphenols.

In an exemplary extraction step, the plant material is dried and ground into a coarse powder and extracted once or twice with from about 50 to about 85% ethanol as a polar solvent (each time from about 10 to about 15 mL solvent per gram of dried tissue). The mix is shaken well and incubated for a time period, such as from about 12 to about 24 hrs at a temperature between about 4° C. to about 20° C. Each time the amount of the solvent is about 10 times the amount of the powder. The extracts are combined and filtered using a Buchner funnel with Whatman filters, and the solution is then brought to room temperature. The pH of the solution may be adjusted as desired and is generally about 7.5.

REFERENCES

Andre C M et al. (2016) *Cannabis sativa*: The plant of the thousand and one molecules. Front Plant Sci 7: 19.
Baron E P (2018) Medicinal properties of cannabinoids, terpenes, and flavonoids in cannabis, and benefits in migraine, headache, and pain: An update on current evidence and cannabis science, headache. J Head Face Pain 58: 1139-1186.
Barrett M L et al. (1985) Isolation from *Cannabis sativa* L. of cannflavin—a novel inhibitor of prostaglandin production. Biochem Pharmacol 34: 2019-2024.
Comelli F. et al. (2008) Antihyperalgesic effect of a *Cannabis sativa* extract in a rat model of neuropathic pain: mechanisms involved. Phytother Res 22: 1017-1024.
Flores-Sanchez I J, Verpoorte R (2008) Secondary metabolism in cannabis. Phytochem Rev 7: 615-639.
Kikuchi H et al. (2019) Chemopreventive and anticancer activity of flavonoids and its possibility for clinical use by combining with conventional chemotherapeutic agents. Am J Cancer Res 9: 1517-1535.
Kumar S, Pandey A K (2013) Chemistry and biological activities of flavonoids: an overview Sci. World J 2013: 162750.
McPartland J M, Russo E B (2014) Non-phytocannabinoid constituents of cannabis and herbal synergy. In: Pertwee, R. G. ed. Handbook of cannabis. Oxford, U.K.: Oxford University Press, 280-295.
Pollastro F et al. (2018) *Cannabis* Phenolics and their Bioactivities. Curr Med Chem 25: 1160-1185.
Rasouli H et al. (2017) Polyphenols and their benefits: A review. Int J Food Properties 20: S1700-S1741.
Rea K A et al. (2019) Biosynthesis of cannflavins A and B from *Cannabis sativa* L. Phytochemistry 164: 162-171.
Shama J et al. (2016) Fruit polyphenols: A review of anti-inflammatory effects in humans. Crit Rev Food Sci Nut 56:419-444.
Watson R S (2014) Polyphenols in plants: Isolation, purification and extract preparation. Academic Press, Oxford, UK.
U.S. Pat. No. 6,403,126
U.S. Pat. No. 9,113,655
U.S. Pat. No. 9,687,469
U.S. Pat. No. 9,730,911
U.S. Patent Application Publication No. 2015/0297653
U.S. Patent Application Publication No. 2018/0098961
U.S. Patent Application Publication No. 2019/0083452
International Patent Application Publication No. WO 2009/043836
International Patent Application Publication No. WO 2016/064987
International Patent Application Publication No. WO 2016/200438
International Patent Application Publication No. WO 2019/056128

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

This example describes a general method for using a PVPP resin and the results in partially purifying cannflavin A.

Figure 1:
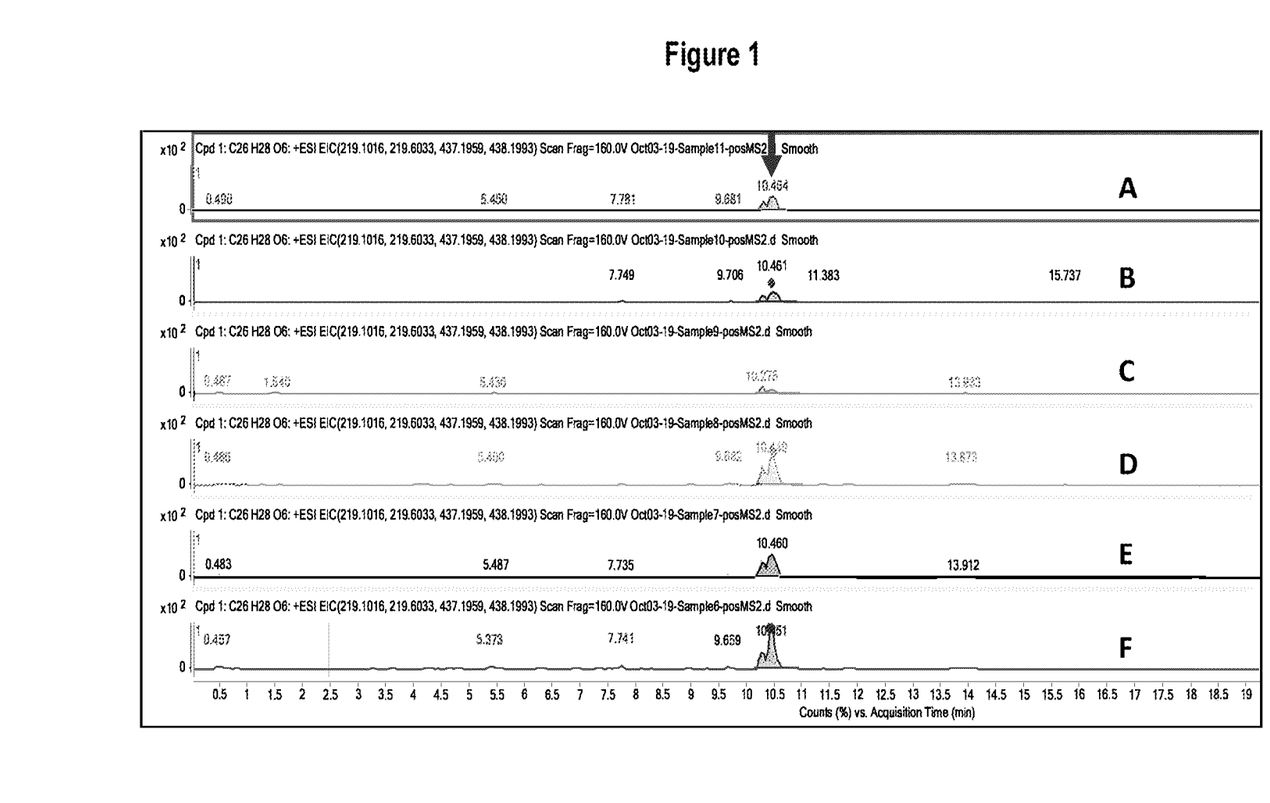
FIG. 1. Chromatograms from LC-MS analyses of cannflavin A present in extracts from hemp stem material obtained using a extraction protocol consisting of initial extraction with 85% EtOH to obtain crude extract samples (A, B, C) and elution from a PVPP resin with 100% ethanol at 45° C. to obtain partially purified samples (D, E. F). The arrow indicates the peak corresponding to the retention time for cannflavin A.

10 g of plant material (hemp stems) were dried in an oven at 65° C. and then powdered using a blender. Ground sample was mixed with 125 mL of 85% EtOH in a glass bottle, was shaken well and was incubated at 4° C. for 18 hours. After that, the extraction mixture was vacuum-filtered using a Buchner filter with Whatman filters (No. 1). The resulting crude extract solution was placed in a 12" hybridization bottle, and 7 g of PVPP was added to every 50 ml of extract and incubated at 25° C. with continuous shaking for 15 minutes. Next, the sample was vacuum filtered and the PVPP was transferred into 35 mL of 100% EtOH for elution and incubated at 45° C. while rotating in a hybridization oven for 20 minutes. The final eluted sample was recovered with vacuum filtration. The samples were subjected to liquid chromatography-mass spectrometry (LC-MS) analysis (FIG. 1). As shown, cannflavin A was detected (average retention time of 10.45 min) in three different initial crude extracts (samples A, B and C) and after elution of the same from the PVPP resin (samples D, E, and F). The average yield of cannflavin A in this example was 0.25 ug/ml of extract.

Example 2

This example describes a general method for using a PVPP resin and the results in partially purifying cannflavin B.

Figure 2:
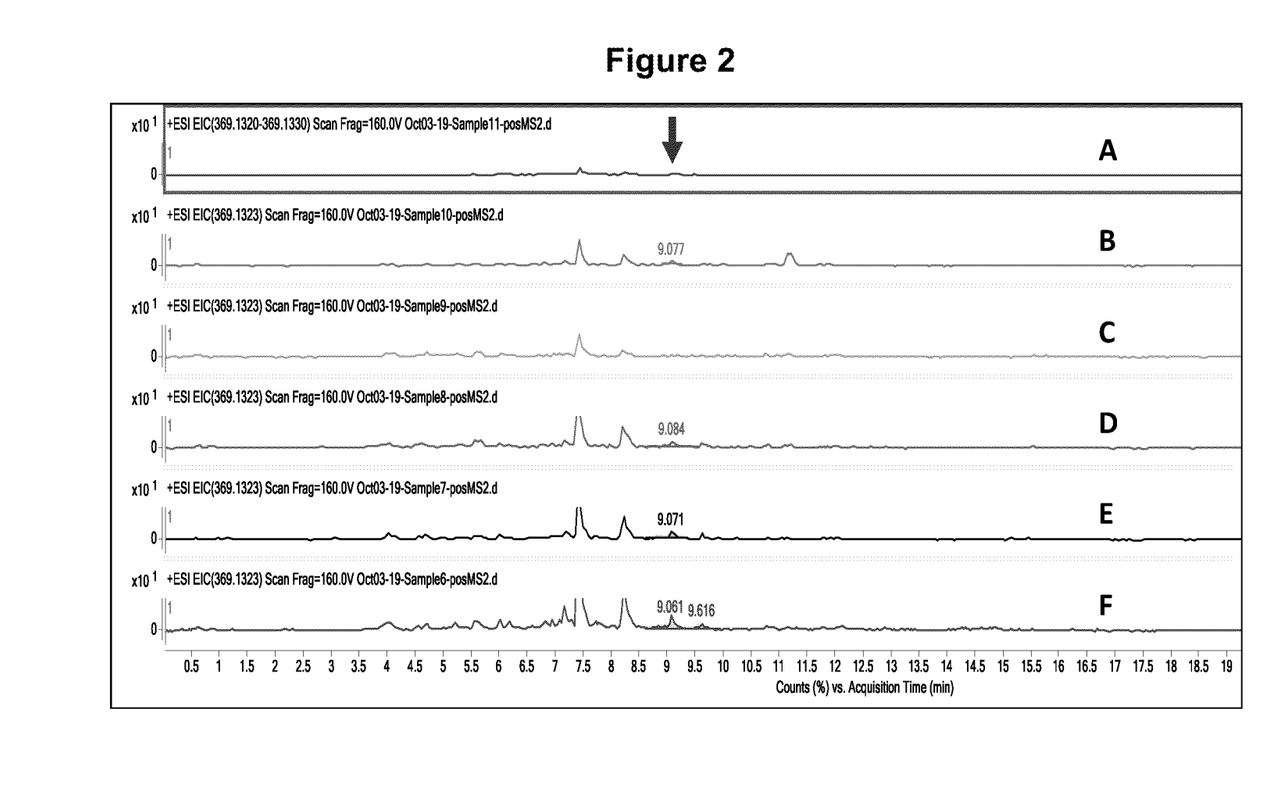
FIG. 2. Chromatograms from LC-MS analyses of cannflavin B present in extracts from hemp stem material obtained using a extraction protocol consisting of initial extraction with 85% EtOH to obtain crude extract samples (A, B, C) and elution from a PVPP resin with 100% ethanol at 45° C. to obtain partially purified samples (D, E. F). The arrow indicates the peak corresponding to the retention time for cannflavin B.

Using a method similar as described above in Example 1, the samples were subjected to liquid chromatography-mass spectrometry (LC-MS) analysis to detect cannflavin B (FIG. 2). As shown, cannflavin B was detected (average retention time of 9.07 min) in one crude extract (sample B) and after elution of samples A, B and C from the resin (samples D, E, and F).

Example 3

This example describes a general method for using a PVPP resin and the results in partially purifying cannflavins and canniprene from a mix of hemp plant material.

10 g of plant material (hemp flowers, leaves and young stems) were dried in an oven at 65° C. and powdered using a blender. Then, the ground sample was extracted using the extraction method as described above in Example 1. Next, the extract was subjected to liquid chromatography-mass spectrometry (LC-MS) analysis to detect cannflavin A (FIG. 3), cannflavin B (FIG. 4), and canniprene (FIG. 5). As shown, cannflavin A, cannflavin B, and canniprene were detected in the crude extract (FIG. 3B, FIG. 4B, and FIG. 5B, respectively) and after elution from the resin (FIG. 3C, FIG. 4C, FIG. 5C, respectively), as determined by the similar retention times and the spectrum mass/charge ratios (m/z) obtained with the standards (FIG. 3A, 4A, 5A, respectively) and expected mass (Table 3).

TABLE 3

Figure 3:
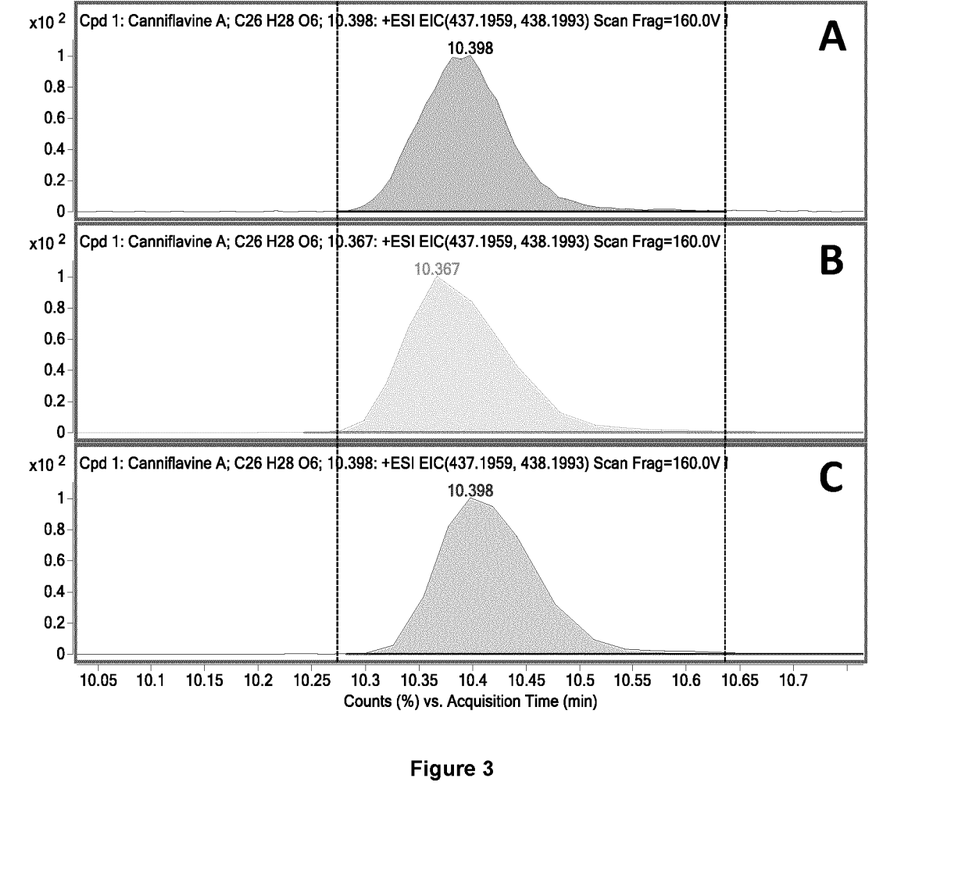
FIG. 3. Chromatograms from LC-MS analyses of cannflavin A present in extracts from a mix of hemp plant material (flower, leaves and young stems) obtained using the described extraction protocol herein. The colored peak corresponds to the retention time for (A) cannflavin A standard, (B) cannflavin A present in the crude extract, and (C) cannflavin A present in the partially purified sample eluted from the PVPP resin.
Figure 4:
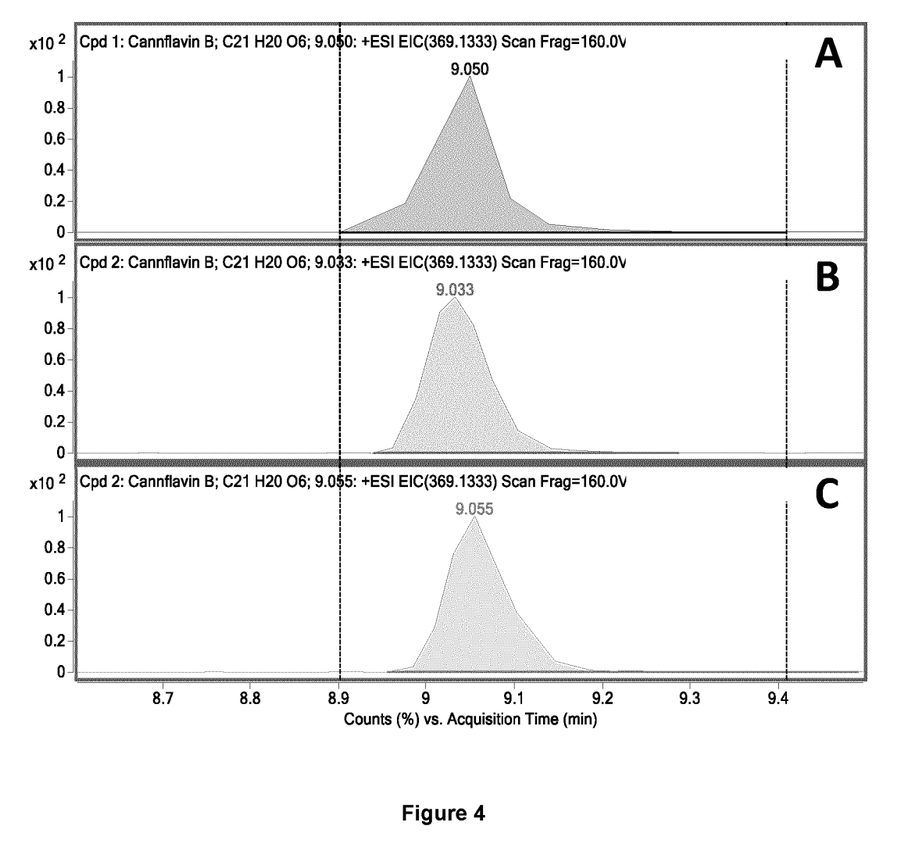
FIG. 4. Chromatograms from LC-MS analyses of cannflavin B present in extracts from a mix of hemp plant material (flower, leaves and young stems) obtained using the described extraction protocol herein. The colored peak corresponds to the retention time for (A) cannflavin B standard, (B) cannflavin B present in the crude extract, and (C) in the partially purified sample eluted from the PVPP resin.
Figure 5:
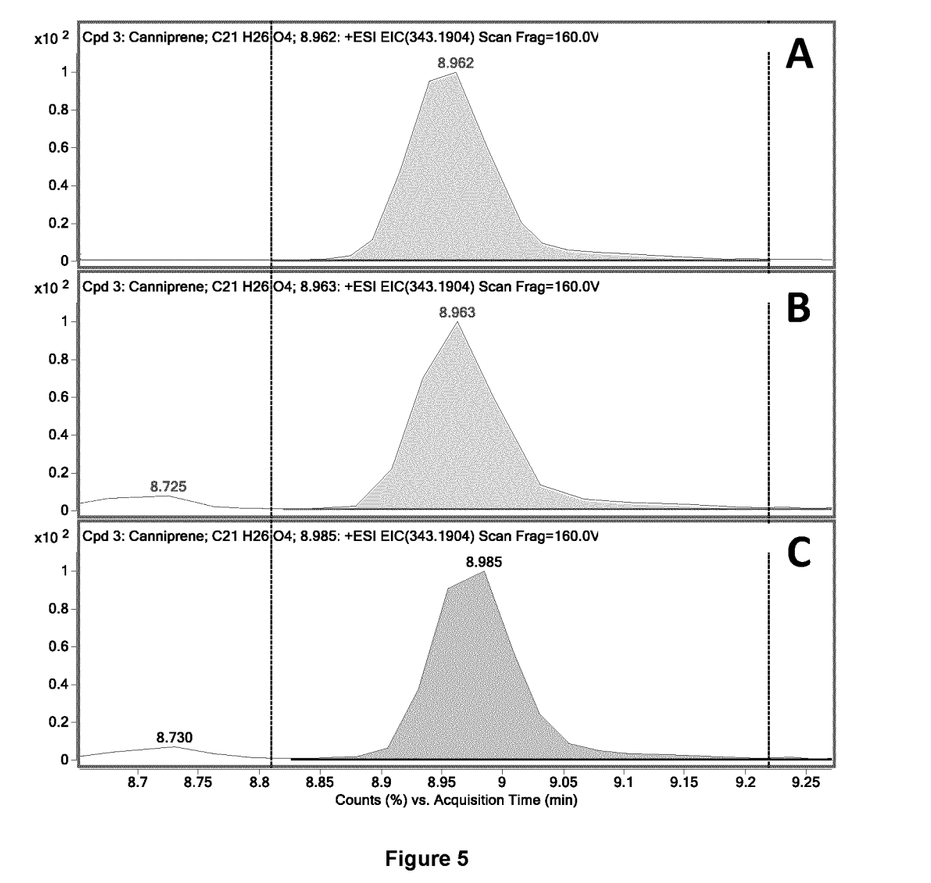
FIG. 5. Chromatograms from LC-MS analyses of canniprene present in extracts from a mix of hemp plant material (flower, leaves and young stems) obtained using the described extraction protocol herein. The colored peak corresponds to the retention time for (A) canniprene standard, (B) canniprene present in the crude extract, and (C) in the partially purified sample eluted from the PVPP resin.

LC/MS data with calculated and observed m/z values for peaks, retention times (RT), and peak area for cannflavin A, cannflavin B and canniprene standards, crude extracts and in eluted extracts after partial purification from a sample described in FIG. 3, FIG. 4 and FIG. 5 (Example 3).

| Compound | Sample | Formula | Mass | RT | m/z | Area |
|---|---|---|---|---|---|---|
| Canniflavin A | Standard | C26 H28 O6 | 436.1870 | 10.398 | 437.1943 | 1476798 |
| | Crude Extract | C26 H28 O6 | 436.1871 | 10.367 | 437.1944 | 9010744 |
| | Eluted | C26 H28 O6 | 436.1855 | 10.398 | 437.1927 | 4493953 |
| Cannflavin B | Standard | C21 H20 O6 | 368.1242 | 9.050 | 369.1315 | 1061496 |
| | Crude Extract | C21 H20 O6 | 368.1249 | 9.033 | 369.1322 | 3556700 |
| | Eluted | C21 H20 O6 | 368.1230 | 9.055 | 369.1302 | 1330440 |
| Canniprene | Standard | C21 H26 O4 | 342.1819 | 8.963 | 343.1887 | 993487 |
| | Crude Extract | C21 H26 O4 | 342.1822 | 8.962 | 343.1893 | 3471522 |
| | Eluted | C21 H26 O4 | 342.1806 | 8.985 | 343.1878 | 1891969 |

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method for producing an eluent enriched with one or more compounds selected from the group consisting of flavonoids, stilbenoids, bibenzyls and combinations thereof, the method comprising:
   a) applying a cannabis extract to a first adsorption resin;
   b) eluting the first adsorption resin to produce a first eluent enriched with one or more compounds selected from the group consisting of flavonoids, stilbenoids, bibenzyls and combinations thereof;
   c) applying the first eluent to a second adsorption resin;
   d) eluting the second adsorption resin to produce a second eluent enriched with one or more compounds selected from the group consisting of flavonoids, stilbenoids, bibenzyls and combinations thereof and wherein the first adsorption resin comprises a macroporous adsorption resin comprising a polymeric non-ionic polystyrene-divinylbenzene resin, and the second adsorption resin comprises polyvinylpyrrolidone.

2. The method of claim 1, wherein the macroporous adsorption resin comprises a polymeric non-ionic polystyrene-divinylbenzene resin selected from the group consisting of SP825, SP207, and XAD-16, and combinations thereof.

3. The method of claim 1, wherein the second eluate is about 3 to about 4 volumes of about 70% to about 100% ethanol.

4. The method of claim 1, wherein the cannabis extract is substantially free of tetrahydrocannabinol.

5. The method of claim 1, wherein the flavonoids are selected from the group consisting of cannflavin A, cannflavin B, and combinations thereof.

6. The method of claim 1, wherein the method further comprises preparing the cannabis extract by extracting cannabis with a polar solvent prior to applying the extract to the adsorption resin.

7. A method for producing an eluent enriched with one or more compounds selected from the group consisting of flavonoids, stilbenoids, bibenzyls and combinations thereof, the method comprising:
   a) applying a cannabis extract to a first adsorption resin;
   b) eluting the first adsorption resin to produce a first eluent enriched with one or more compounds selected from the group consisting of flavonoids, stilbenoids, bibenzyls and combinations thereof;
   c) applying the first eluent to a second adsorption resin;
   d) eluting the second adsorption resin to produce a second eluent enriched with one or more compounds selected from the group consisting of flavonoids, stilbenoids, bibenzyls and combinations thereof and wherein the first adsorption resin comprises polyvinylpyrrolidone and the second adsorption resin comprises a macroporous adsorption resin comprising a polymeric non-ionic polystyrene-divinylbenzene resin.

8. The method of claim 7, wherein the macroporous adsorption resin comprises a polymeric non-ionic polystyrene-divinylbenzene resin selected from the group consisting of SP825, SP207, and XAD-16, and combinations thereof.

9. The method of claim 7, wherein the first eluate is about 3 to about 4 volumes of about 70% to about 100% ethanol.

10. The method of claim 7, wherein the cannabis extract is substantially free of tetrahydrocannabinol.

11. The method of claim 7, wherein the flavonoids are selected from the group consisting of cannflavin A, cannflavin B, and combinations thereof.

12. The method of claim 7, wherein the method further comprises preparing the cannabis extract by extracting cannabis with a polar solvent prior to applying the extract to the adsorption resin.

* * * * *